United States Patent [19]

Kowalski

[11] 4,097,747

[45] Jun. 27, 1978

[54] DEVICE FOR MEASURING ABSORPTION OF RADIATION IN A SLICE OF A BODY

[75] Inventor: Günter Kowalski, Hamburg, Germany

[73] Assignee: U.S. Philips Corporation, New York, N.Y.

[21] Appl. No.: 761,452

[22] Filed: Jan. 21, 1977

[30] Foreign Application Priority Data

Feb. 3, 1976 Germany .............................. 2604020

[51] Int. Cl.² ............................................ G03B 41/16
[52] U.S. Cl. ................................. 250/445 T; 250/514
[58] Field of Search .................... 250/445 T, 505, 514

[56] References Cited

U.S. PATENT DOCUMENTS 3,922,552  11/1975  Ledley ............................ 250/445 T

*Primary Examiner*—Craig E. Church

*Attorney, Agent, or Firm*—Frank R. Trifari

[57] ABSTRACT

In third-generation computer tomography apparatus measuring values must be intermediately stored partly for the total scanning time in order to enable processing of all measuring values with a given projection angle. This involves high expenditures for storage means. Moreover, the applied dose is larger than required for obtaining the measuring value per se.

The invention consists in that there is provided a shield which moves with the radiator but whose direction does not change in space during the measurement, but does change relative to the radiation beam. As a result, it is achieved that all measuring values with a given projection angle can be obtained within a part of the scanning time, the said part corresponding to the ratio between the opening angle of the radiation beam and the total scanning time. As a result, the cost of intermediate storage as well as the patient dose can be reduced.

4 Claims, 9 Drawing Figures

DEVICE FOR MEASURING ABSORPTION OF RADIATION IN A SLICE OF A BODY

The invention relates to a device for measuring radiation absorption in a slice of a body, comprising a radiator which emits a fan-shaped radiation beam which completely envelops a body to be examined, an array of detectors, arranged behind the body, for measuring local radiation intensity, and a movement mechanism for rotating the radiator/detector system during a measurement.

A device of this kind is known, for example, from German Offenlegungsschrift No. 2,434,224. The absorption values measured by the array of detectors, each of which is a measure for the absorption of the radiation along a trajectory given by the position of the radiator and the relevant detector during this measurement, are utilized, for example, for calculating the absorption of the radiation in various points of a slice of a body to be examined.

Because the fan-shaped radiation beam envelops the complete body to be examined in each position of a radiator/detector system, the radiator/detector system need only be rotated during a measurement. Consequently, a measurement of this kind can be performed substantially faster than in a device as described, for example, in German Offenlegungsschrift No. 19,41,433, in which a single radiation detector is used; this detector measures only a very narrow strip-shaped radiation beam of the radiator and must be shifted perpendicularly to the direction of the strip for measuring the total area to be examined, before the radiation/detector system is shifted through a small angular increment, for example 1°, after which the same operation is repeated. In practice the time required for a complete measurement using a device of the kind set forth, for example, amounts to a few seconds, while this time amounts to a few minutes when use is made of a device as described in the German Offenlegungsschrift No. 19,41,433.

However, there are also drawbacks. For example, as appears from German Offenlegungsschrift 1,941,433, the reconstruction of the absorption of the radiation in the plane of examination each time requires the measuring values measured along parallel beam paths through the area examined. When use is made of the device described in the German Offenlegungsschrift No. 1,941,433, this measuring value is obtained by shifting the radiator/detector system perpendicularly to the beam path in a direct time succession. In the known devices, however, where the overall area to be examined is covered by the fan-shaped radiation beam, the absorption is measured along parallel beam paths at different instants of the measurement or in different angular positions of the radiator/detector system. Consequently, these values must be intermediately stored, which necessitates the use of a large number of intermediate stores.

This aspect will be described in detail hereinafter with reference to FIG. 1 which diagrammatically shows the geometrical configuration in a device of the kind set forth. Therein, the radiator is denoted by the reference 1, the group of radiation detectors by the reference 2, the centre of rotation by the reference 3, and the slice of the body to be examined by the reference 4. A fan-shaped radiation beam is bounded by the rays 5 and 6. It is assumed that the radiator/detector system is rotated through an arc of a circle 7 about a centre of rotation during the measurement in the direction of the arrow, i.e., clockwise. In a starting position a measuring value is obtained which is a measure for the absorption along a radiation path $a$ extending vertically through the center of rotation. When the radiator/detector system is subsequently rotated slightly, the absorption can also be measured along a beam path $b$ which is situated to the right of the center of rotation. The absorption along the beam path $c$ which is situated to the left of the center of rotation, however, is measured only when the radiator/detector system has been rotated through more than 180°. This means that the measuring values obtained along the beam paths $a$ and $b$ must be stored for at least the relevant measuring time required, which causes a substantial cost increase due to the stores required.

A further drawback exists in that the patient is exposed to a radiation dose which is larger than required for obtaining the necessary absorption values per se; notably when the scanning angle, i.e., the maximum angle between two sets of parallel extending beam paths, amounts to only 180°. The part of the radiation which is not required for the measurement then relates to the part which is required for the measurement as the opening angle $\alpha$ of the fan-shaped radiation beam relates to the applicable scanning angle.

The invention has for its object to provide a device of the kind set forth in which the expenditures for intermediate storage are substantially reduced and in which the radiation dose is also reduced, at least for scanning angles of approximately 180° and slightly higher.

In accordance with the invention a shielding device moves with the radiator in a translatory manner during the measurement and which is not rotated, at least for as long as it is present in the beam path, the angle of rotation of the radiator/detector system being equal to the sum of the scanning angle and the opening angle of the fan-shaped radiation beam. It is to be noted that all devices of the kind set forth comprise a shielding device which moves along with the radiator during the measurement and which stops the beam to be fan-shaped. This shielding device, however, is rigidly connected to the radiator and thus moves as an integral unit so that the orientation thereof, continuously varies in space. A device in accordance with the invention may also comprise such a shielding device.

A preferred embodiment in accordance with the invention for devices in which the scanning angle is between 180° and 360° − $\alpha$, comprises a single shield which shields an angular region which corresponds to 360° − $\alpha$ or slightly less, but not less than the opening angle of the fan-shaped radiation beam. This embodiment is particularly simple, because only a single shield is required.

In a further preferred embodiment, the shielding device is rotatable about an axis which is perpendicular relative to the plane of examination and which extends through the center of the radiator, means being provided which rotate the shielding device about the axis at the same angular velocity, but in the opposite direction of rotation, as that at which the radiator/detector system is rotated about the center of rotation. This further embodiment represents a particularly simple version in accordance with the invention, which enables the shielding device to be moved along with the radiator in a translatory manner without the angular position thereof in space being changed; however, this change does occur relative to the fan-shaped radiation beam.

In a further preferred embodiment of the invention, a first shield having a first angular position in space is slid into the plane of examination during a first half of the measurement. During the second half of the measurement a second shield is slid into the plane of examination, an opening angle of 360° − β being between the two facing shield edges. This embodiment can also be used for scanning angles which are smaller than 360° − α, but it is particularly advantageous when used for larger scanning angles. The use of the terms a "first" and a "second" shield does not necessarily imply that different shields are concerned. A single shield which is abruptly placed in another angular position after the first half of the measurement can also be used. This device can in principle also be used for scanning angles larger than 360°. In that case, after an 180° rotation a change-over between the two shields, or a change-over of the one shield from a first position to a second position must take place.

Some preferred embodiments in accordance with the invention will be described in detail hereinafter with reference to the drawing.

Figure 3:
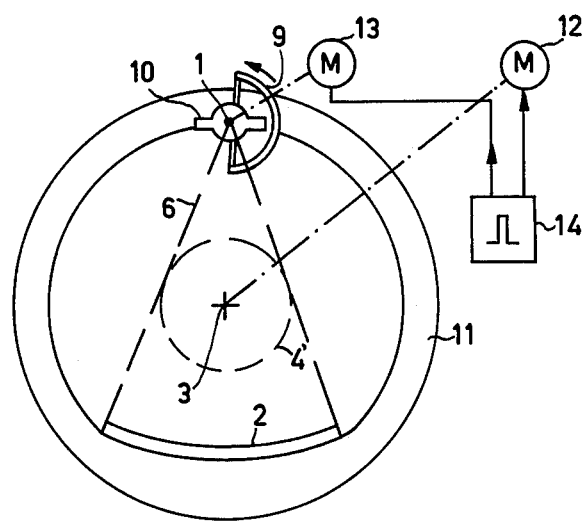
Figure 4A:
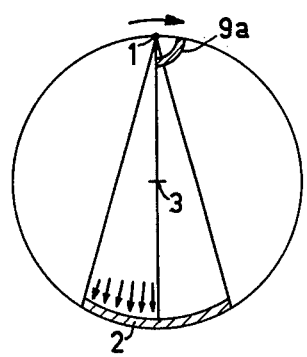
Figure 4B:
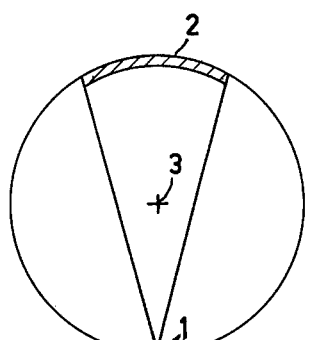
Figure 4C:
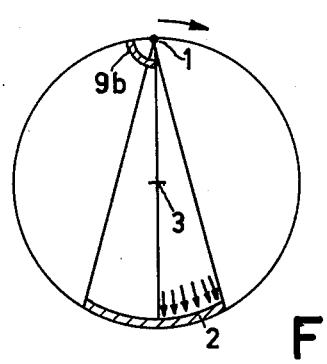

FIG. 3 diagrammatically shows the construction of such a device,

FIGS. 4a to 4c show the geometrical relationships in a device in accordance with the invention for a scanning angle of 360°.

Figure 1:
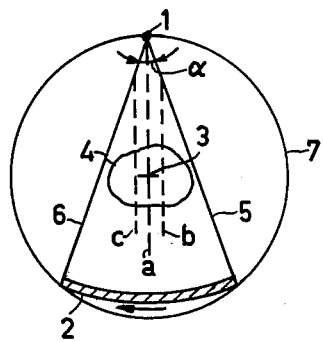
FIG. 1 shows a prior art device

In the FIGS. 2a to 2b, 3 and 4a to 4c use is made of the references used in FIG. 1 for corresponding elements.

Figure 2A:
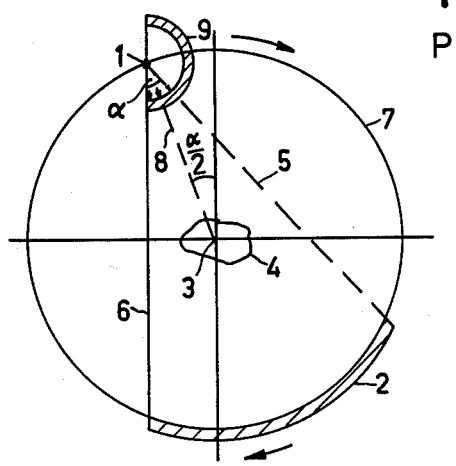
FIGS. 2a to 2d show the geometrical relationships in a device in accordance with the invention, in which the scanning angle amounts to only 180°, in different phases of the measurement.

FIG. 2a shows a radiator/detector system in the starting position at the beginning of a measurement. A shield (not shown) which is rigidly connected to the radiator forms a fan-shaped radiation beam having the opening angle α and boundary lines 5 and 6. In this position a connecting line 8 between the radiator 1 and the center of rotation 3 encloses an angle α/2 with the vertical line. In accordance with the invention, there is provided a shield 9 which orbits with the radiator in a translatory manner, but without its orientation in space being changed. However, a change in orientation does occur relative to the fan-shaped radiation beam. This shield shields an angular region of 180°, so that the total half space (to the right of the vertical line in the drawing) is shielded. In the starting position the overall radiation of the radiator is shielded by the shield 9, with the exception, however, of the radiation along the boundary line 6. When the radiator is rotated clockwise, a part of the radiation which continuously increases as the angle of rotation increases reaches the part of the body 4 present in the plane of examination.

Figure 2B:
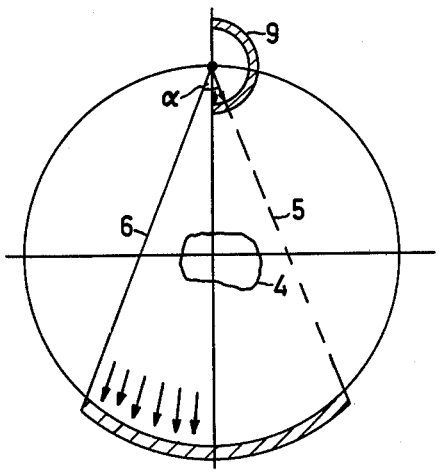

FIG. 2b shows the device after the radiator/detector system has been rotated through the angle α/2, i.e., half the opening angle of the fan-shaped radiation beam. The one half of the radiation beam is then shielded by the shield 9, while the other half can pass the shield to reach the body 4.

Figure 2C:
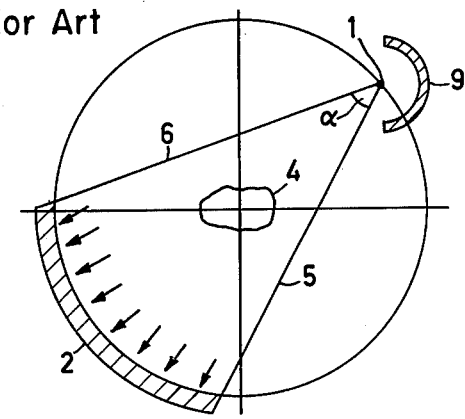

After the radiator/detector system has been rotated through at least the angle α, the total fan-shaped radiation beam of the radiator 1 can reach the body 4; in this phase of the measurement, shown in FIG. 2c, the shield 9 is no longer effective. When the radiator/detector system is rotated further, the boundary 6 first reaches the edge of the shield 9. If the radiator/detector system is rotated further the shielded part of the radiation increases as the angle of rotation increases until the end position (FIG. 2d) the total radiation is shielded by the shield 9.

Even through the radiator/detector system is rotated through an angle of 180° + α during a measurement, measuring values are then obtained which represent the absorption of the radiation along beam paths which intersect at an angle of maximum 180°. The scanning angle thus amounts to only 180°, i.e., the angle of rotation equals the sum of the opening angle of the beam and the scanning angle.

An advantage of the device in accordance with the invention consists in that all measuring values which represent the absorption along parallel extending beam paths are obtained during a rotation of the radiator/detector system through the angle α. This is applicable to all directions. For example, the measuring values along vertically extending beam paths to the left of the center 3 are obtained during the first phase, i.e., between the position shown in FIG. 2a and the position shown in FIG. 2b. The measuring values along the parallel extending vertical beam paths to the right of the center are completely obtained when the radiator/detector system is rotated further through the angle α/2. All measuring values along vertical beam paths are thus obtained already during the first part of the measurement which corresponds to the angle of rotation α. They can then be further processed for reconstruction and need no longer be intermediately stored, so that the cost of intermediate storage can be reduced.

It can be demonstrated that the prior art devices of the kind set forth, which do not include a shielding device in accordance with the invention, require an angle of rotation of 180° + α for scanning the object to be examined in an angular region of 180° (this angular region is required for the complete scanning). During the rotation of the radiator/detector system, the radiation then passes through the entire region to be examined. According to the invention an angle of rotation of 180° + α is also required for obtaining the measuring values in an angular region of 180°. However, the area to be examined is only partly exposed to the radiation of the radiator during the initial phase (FIGS 2a and 2b) and during the end phase (FIG. 2c) of the measurement. As a result, the dose whereto the patient is subjected during the measurement is reduced.

Figure 2D:
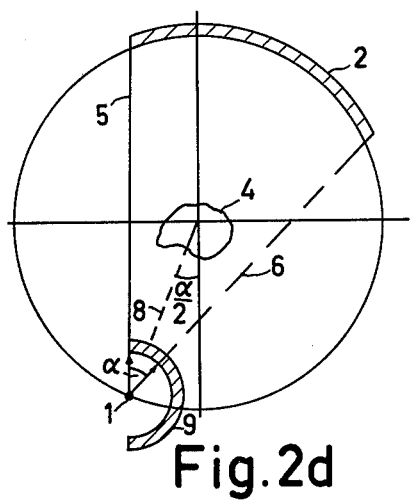

When the radiator/detector system is rotated through the position shown in FIG. 2d (as far as the starting position of FIG. 2a), without the radiation being switched off, the radiation load on the patient is not increased; however, no further measuring values are obtained either. Therefore, it would in principle be possible to start the measurement in an arbitrary position of the radiator/detector system and to execute a rotation of 360° about the center of rotation. The measurement would then be prolonged, so that in given circumstances intermediate storage for more than one half rotation would be required. Therefore, the starting position of the radiator/detector system is preferably so chosen, or the shielding device 9 is preferably so positioned, that the total radiation is shielded by the shield 9 at the beginning of the measurement (as in FIG. 2a), the opening angle of the radiation beam passed by the shield 9 subsequently is increased, as the angle of rotation increases, to the same extent as the angle of rotation of the radiator/detector system, until the shielding device is no longer effective in the beam path. When the radiator/detector system is rotated clockwise about the center of rotation, this can be achieved by arranging the shield 9 so, or by choosing the starting position so, that the left beam boundary (viewed from the group of detectors) coincides with a shield edge, the total remaining beam being shielded by the shielding device. When the radiator/detector system is rotated counter-clockwise about the center of rotation, the right beam boundary ray should coincide with a shield edge.

FIG. 3 diagrammatically shows an embodiment of a device in accordance with the invention with a scanning angle of 180°, in the same phase as shown in FIG. 2b. The radiator 1 is formed by the focus of an X-ray radiator 10 which is mounted on a circular yoke 11 on which a group of detectors 2 is arranged on the opposite side. The yoke 11 is rotated by means of a step motor 12, in a manner not shown, about an axis which extends through the center of rotation 3, perpendicular to the plane of the drawing. A further step motor 13 rotates the sheild 9, again in a manner not shown, about a parallel extending axis through the radiator 1. This motor is rigidly connected to the yoke 11. The step motors 12 and 13, are controlled together by a pulse generator 14, and are constructed so that in reaction to each control pulse the shield 9 and the yoke 11 are rotated through the same angle; however, the yoke 11 is rotated clockwise while the shield 9 is rotated counter-clockwise (or vice versa). Thus, the direction of the shield 9 in space is fixed, so that it does not rotate with the tube 10, even though it is moved with this tube in a translatory manner. The rotation of the shield 9 about the axis extending through the radiator 1, in synchronism with but in the opposite direction from the rotation of the yoke 11 about the center of rotation 3, can in principle also be obtained by adapted drives.

Even though the invention has been described with reference to the FIGS. 2 and 3 for a scanning angle of 180°, it can also be used in devices of the kind set forth with larger scanning angles. If this scanning angle is denoted by the reference $\beta$, the radiator/detector system or (FIG. 3) the yoke 11 must be rotated through an angle $\beta + \alpha$ about the center of rotation 3. The shield 9 would then have to shield an angle of $360° - \beta$. However, the opening angle will preferably be chosen to be slightly larger in order to eliminate edge effects which are caused, for example, by a radiation source which is not a point. The shielded angular region becomes smaller than when the angle $360° - \beta$ is smaller than $\alpha$. This would mean that in the starting or the end position the total fan-shaped radiation beam can no longer be covered by the shielding device; therefore, the invention can no longer be realized using only one shield.

In view of obtaining a solution for these cases, it is to be noted that actually only part of the shield 9 as shown in the FIGS. 2a and 2d and FIG. 3 is effective, i.e., the part which starts near the lower shielding edge and extends over the opening angle $\alpha$ and which influences the beam path at the beginning of the measurement (see FIGS. 2a and 2b), and the upper part which starts at the upper shield edge and extends over the angular region $\alpha$ and which is effective in the beam path during the end phase of the measurement. The intermediate part of the shield 9, therefore, is not at all required and may, therefore, be made, for example, of a radiation transmitting material.

It is also to be noted that at anytime only one of these two shield parts is effective in the beam path. Consequently, only one shield part need be present, so that the upper part of the shield 9 could be completely omitted in the starting phase, while the lower part could be omitted in the end phase. Therefore, in the transition phase, for example, after half the measurement has been completed, or in the phase shown in FIG. 2c, the upper shield part could readily be positioned in the beam path and the lower shield part could be withdrawn from the beam path. This would imply a rotation of a shield part (and indeed a single shield part could be brought from the lower position to the upper position in the transition phase but this rotation does not take place as long as this shield part is present in the beam path.

It is also to be noted that an opening angle of 180° exists between the lower edge of the shield 9, which ultimately leaves the beam path in the starting phase, and the upper edge of the shield 9. This angle exactly corresponds to the scanning angle. Thus, the following possibilities exist:

(a) The shielding device consists of two shields, each of which each time shields an angular region which corresponds to the opening angle of the fan-shaped radiation beam (the shielding angle may in principle also be larger, but may not be too large). At the beginning of the measurement only one of the shields is present in the plane of examination. In the transition phase, notably after half the measurement has been completed, this shield is withdrawn from the plane of examination and the other shield penetrates increasingly further in the plane of examination. The angle between the edge of the one shield which is last present in the beam path and the edge of the other shield which is first present in the beam path amounts to $360° - \beta$ ($=$ scanning angle).

(b) Use is made of only a single shield with the scanning angle. During the first phase of the measurement, this shield is arranged in the beam path so that at the beginning of the measurement the fan-shaped radiation beam is completely shielded thereby, the fan-shaped beam being increasingly allowed to pass upon rotation of the radiator/detector system. In the transition phase, the shield is abruptly displaced to a second position, so that angle between the edge of the shield which disappears last from the beam path during the starting phase and the edge of the shield which arrives first in the beam path during the end phase after the change of the position, corresponds to the angle $360° - \beta$.

The FIGS. 4a and 4c show these possibilities for an embodiment of a device in accordance with the invention with a scanning angle of 360°. FIG. 4a shows the device in the starting phase after the radiator/detector system has been rotated through the angle $\alpha/2$. The shield 9a shields exactly half the radiation, like in FIG. 2b. FIG. 4b shows the geometrical relationships after half the measurement has been completed. The shield 9a is withdrawn, as is denoted by broken lines, from the plane of examination and a shield 9b is slid into the plane of examination. The left edge of the shield 9a, last leaving the beam path during the starting phase, and the right edge of the shield 9b, which first arrives in the beam path after further rotation of the radiator/detector system, enclose an opening angle of 0° relative to the radiator 1 (i.e., $360° - \beta$).

The changing of the shields 9a and 9b should not be effected exactly halfway of the measurement. This can be effected earlier or later, but not when one of the two shields is completely or partly present in thebeam path. FIG. 4b shows that instead of two shields, which are interchanged in a given phase of the measurement, use can alternatively be made of a single shield which can be rotated, for example, in the phase shown in FIG. 4b, from the position 9a to the position 9b. FIG. 4c shows the geometrical relationships briefly before the completion of the measurement. The shield 9b already shields half the fan-shaped radiation beam again (in this case the left half).

What is claimed is:

1. A device for measuring radiation absorption in a slice of a body, comprising a radiator which emits a fan-shaped radiation beam which completely envelops a body to be examined, an array of detectors, arranged behind the body, for measuring local radiation intensity, a movement mechanism for rotating the radiator/detector system during a measurement, and shielding means which moves with the radiator in a translatory manner during the measurement and whose orientation in space is not rotated, at least for as long as it is present in the beam path, the angle of rotation of the radiator/detector system being equal to the sum of the scanning angle ($\beta$) and the opening angle ($\alpha$) of the fan-shaped radiation beam.

2. A device as claimed in claim 1, in which the scanning angle ($\beta$) is between 180° and (360° − $\alpha$), wherein the shielding means comprises a single shield (9) which shields an angular region which corresponds to 360° − $\beta$ or slgihtly less, but not smaller than the opening angle ($\alpha$) of the fan-shaped radiation beam.

3. A device as claimed in claim 1, wherein the shielding means (9) is rotatable about an axis which is perpendicular to the plane of examination and which extends through the center (focus) of the radiator (1), there being provided means (12, 13, 14) for rotating the shielding means about the axis at the same angular velocity, however in the opposite direction, as that at which the radiator/detector system is rotated about the center of rotation (3).

4. A device as claimed in claim 1, for a scanning angle ($\alpha$) which is larger than (360° − $\alpha$), wherein during the first half of the measurement a first shield (9a), having a first angular position in space, is slid into the plane of examination and during the second half of the measurement a second shield (9b) is slid into the plane of examination, an opening angle of (360° − $\beta$) existing between the facing edges of the shields.

* * * * *